United States Patent [19]

Warriner

[11] Patent Number: Plant 6,069

[45] Date of Patent: Dec. 29, 1987

[54] ROSE PLANT JACEL

[75] Inventor: William A. Warriner, Tustin, Calif.

[73] Assignee: Jackson & Perkins Company, Medford, Oreg.

[21] Appl. No.: 817,552

[22] Filed: Jan. 10, 1986

[51] Int. Cl.[4] ..... A01H 5/00

[52] U.S. Cl. ..... Plt./15

[58] Field of Search ..... Plt./15

*Primary Examiner*—James R. Feyrer

*Attorney, Agent, or Firm*—Manford R. Haxton

[57] ABSTRACT

A hybrid tea rose variety having heavy production of bright yellow buds and flowers fringed with long bearded sepals, round undulating petals and possessing very little fragrance.

1 Drawing Figure

This present invention relates to a new and distinct variety of rose plant of the hybrid tea class which was originated by crossing the variety New Day, U.S. Plant Pat. No. 3,228, with an unnamed variety.

The primary objective of this breeding was to produce a new rose variety of the hybrid tea class with bright yellow flowers, very free blooming and vigorous, erect plant habit. This objective was substantially achieved along with other desirable improvements as evidenced by the following unique combination of characteristics which are outstanding in the new variety and which distinguish it from its parents as well as from all other varieties of which I am aware:

1. Intense bright yellow buds and one day open flowers;
2. Heavy and continuous flower production;
3. Long bearded sepals;
4. Round flat to slightly undulated petals; and
5. Little fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—New Day, U.S. Plant Pat. No. 3,228.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in September, 1985.

Blooming habit: Continuous.

Bud:

*Size.*—1¼" to 1½" when petals start to unfurl.

*Form.*—Pointed ovoid.

*Color.*—When sepals first divide, a very deep yellow. Yellow Group 13A often showing green vegetative coloration on the outer petals; when half blown, upper side of petals bright yellow, Yellow Group 12A to 12B; lower side of petals bright yellow, Yellow Group 12A to 12B.

*Sepals.*—Color: Green Group 143A. Three appendaged sepals normally to heavily appendaged. Two unappendaged sepals hairy edge.

*Receptacle.*—Color: Green Group 143A. Shape: Flattened funnel. Size: Medium. Surface: Smooth.

*Peduncle.*—Length: Medium. Surface: Prickly and glandular. Color: Medium green. Strength: Stiff.

Open Bloom:

*Size.*—Medium. Average open size 3"-3½".

*Borne.*—Singly to several together.

*Stems.*—Medium, strong.

*Form.*—When first open, high center. Permanence: Retains its form to the end.

*Petalage.*—Number of petals under normal conditions: 30-33.

*Color.*—Center of flower: Upper side of petals, yellow, Yellow Group 12A to 12B; reverse side of petals, yellow, Yellow Group 12A to 12B. Base of petals, same or slightly more intense Yellow Group 13A.

*Discoloration.*—General tonality at end of first day: Little change. Third day: Gradual fading of the yellow to Yellow Group 12C.

*Fragrance.*—Slight.

Petals:

*Texture.*—Thick.

*Shape.*—Round.

*Form.*—Flat to slightly undulated.

*Arrangement.* —Imbricated. Petaloids in center, few.

*Persistence.*—Drop off cleanly.

*Lastingness.*—On the plant, long. As cut flower, long.

Reproductive parts:

*Anthers.*—Large. Color: Yellow Arrangement: Regular around styles.

*Filaments.*—Color: Yellow.

*Pollen.*—Gold yellow.

*Styles.*—Color: Red.

*Stigmas.*—Color: White.

PLANT

Form: Bush.
Growth: Vigorous.
Foliage:
*Number of leaflets on normal mid-stem leaves.*—5.
*Size.*—Medium.
*Quantity.*—Abundant.
*Color.*—New Foliage: Reddish. Old Foliage: Green Group 139A.
Leaflets:
*Shape.*—Oval pointed.
*Texture.*—Smooth.
*Edge.*—Serrated.
*Serration.*—Single.
*Petiole.*—Rachis: Color: Reddish. Underside: Rough with prickles.
*Stipules.*—Long, bearded.
*Disease resistance.*—Susceptible to mildew, under normal growing conditions at Irvine, Calif.

Wood:
*New wood.*—Color: Light green. Bark: Smooth.
*Old wood.*—Color: Green. Bark: Smooth.
Prickles:
*Quantity.*—On main canes from base: Ordinary. On laterals from main canes: Ordinary.
*Form.*—Long, straight.
*Color when young.*—Red.
Small prickles:
*Quantity.*—On main stalks, few. On laterals, few.
*Color.*—Reddish green to green.

I claim:

1. A new and distinct variety of rose plant of the hybrid tea class, substantially as herein shown and described, characterized particularly as to novelty by the unique combination of heavy production of bright yellow buds and flowers fringed with long bearded sepals, round undulating petals and possessing very little fragrance.

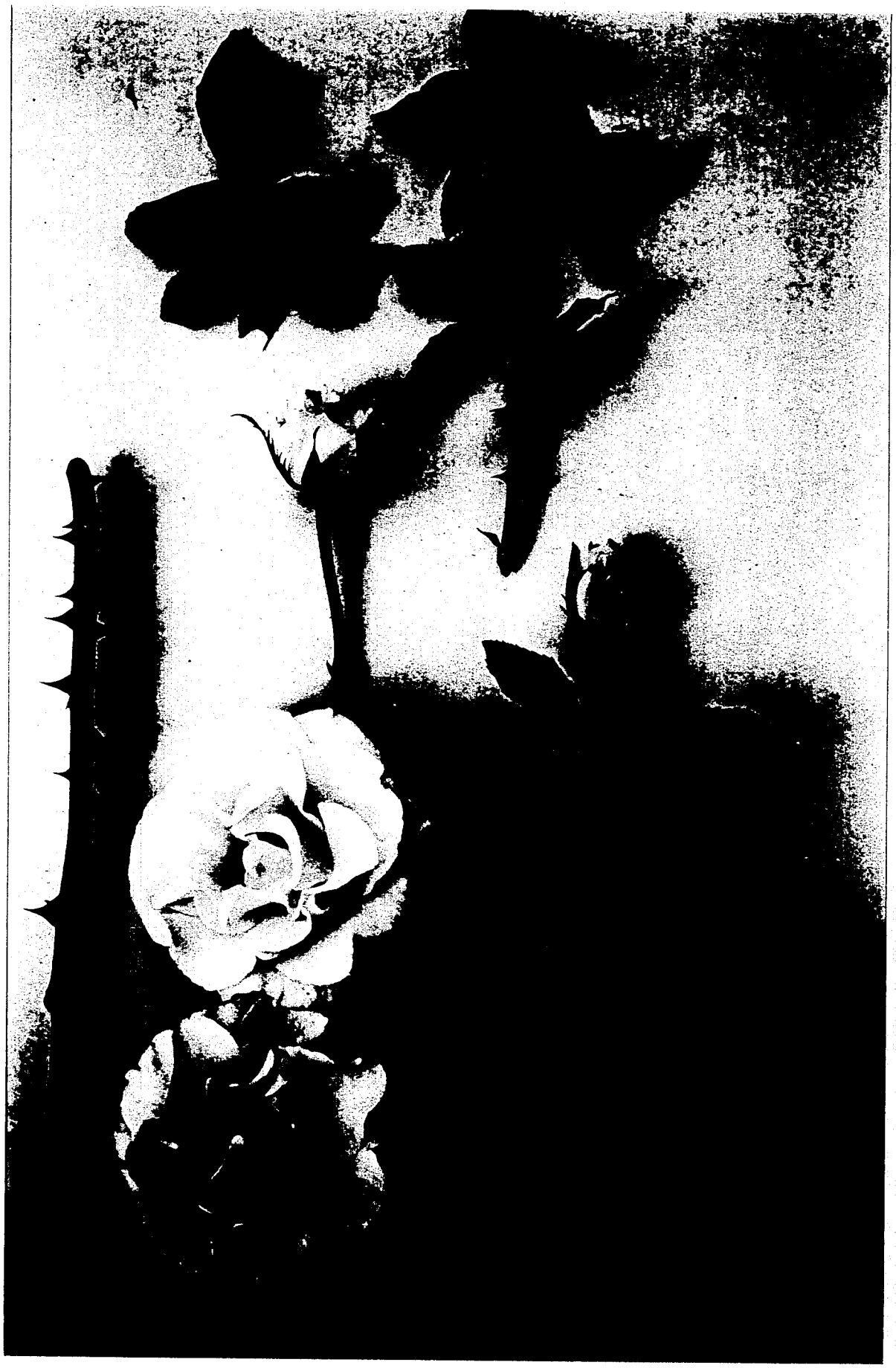

* * * * *